United States Patent
Jeffs et al.

(10) Patent No.: US 9,327,031 B2
(45) Date of Patent: *May 3, 2016

(54) BUFFER SOLUTIONS HAVING SELECTIVE BACTERICIDAL ACTIVITY AGAINST GRAM NEGATIVE BACTERIA AND METHODS OF USING SAME

(71) Applicant: United Therapeutics Corporation, Silver Spring, MD (US)

(72) Inventors: Roger Andrew Jeffs, Chapel Hill, NC (US); David Zaccardelli, Cary, NC (US)

(73) Assignee: United Therapeutics Corporation, Silve Spring, MD (US)

( * ) Notice: Subject to any disclaimer, the term of this patent is extended or adjusted under 35 U.S.C. 154(b) by 5 days.

This patent is subject to a terminal disclaimer.

(21) Appl. No.: 14/158,091

(22) Filed: Jan. 17, 2014

(65) Prior Publication Data

US 2014/0194520 A1    Jul. 10, 2014

Related U.S. Application Data

(63) Continuation of application No. 13/912,753, filed on Jun. 7, 2013, now Pat. No. 8,653,137, which is a continuation of application No. 13/022,005, filed on Feb. 7, 2011, now Pat. No. 8,658,694, which is a (Continued)

(51) Int. Cl.
| | |
|---|---|
| *A61K 31/198* | (2006.01) |
| *A61K 31/5575* | (2006.01) |
| *A61K 47/18* | (2006.01) |
| *A61K 9/00* | (2006.01) |
| *A61K 47/02* | (2006.01) |

(52) U.S. Cl.
CPC .............. *A61K 47/18* (2013.01); *A61K 9/0019* (2013.01); *A61K 31/5575* (2013.01); *A61K 47/183* (2013.01); *A61K 47/02* (2013.01)

(58) Field of Classification Search
None
See application file for complete search history.

(56) References Cited

U.S. PATENT DOCUMENTS

| 4,008,759 A | 2/1977 | Blackwell |
| 4,335,139 A | 6/1982 | Watts et al. |
| 5,153,222 A | 10/1992 | Tadepalli et al. |
| 2002/0177611 A1* | 11/2002 | McShane et al. ............. 514/338 |
| 2009/0088468 A1 | 4/2009 | Palepu |

FOREIGN PATENT DOCUMENTS

| EP | 0 347 243 B1 | 1/1993 |
| JP | 02-040325 A | 2/1990 |

(Continued)

OTHER PUBLICATIONS

Task Force Members: Nazzareno Galie et al., "Guidelines on diagnosis and treatment of pulmonary arterial hypertension—The Task Force on Diagnosis and Treatment of Pulmonary Arterial Hypertension of the European Society of Cardiology," European Hearth Journal, 2004, 25:2243-2278.

Barst, R., "A Comparison of Continuous Intravenous Epoprostenol (Prostacyclin) with Conventional Therapy for Primary Pulmonary Hypertension," *The New England Journal of Medicine*, vol. 334, No. 5, pp. 296-301 (1996).

Catalano, et al, "Incidence of Salmonella in Pennsylvania Egg Processing Plants and Destruction by High pH," *J. Food Prot.*, vol. 57, pp. 587-591 (1994).

(Continued)

*Primary Examiner* — Abigail Fisher
*Assistant Examiner* — Jessica Kassa
(74) *Attorney, Agent, or Firm* — Foley & Lardner LLP

(57) ABSTRACT

Buffer solutions for pharmaceutical preparations that have bactericidal activity preferentially against gram negative bacteria are provided. The buffers have a pH of greater than about 10 or less than about 4.5 with low buffer capacity. Methods of their use in reducing the occurrence of blood stream infections in a mammal is also provided.

14 Claims, 15 Drawing Sheets

Related U.S. Application Data continuation of application No. 12/276,707, filed on Nov. 24, 2008, now Pat. No. 7,999,007, which is a continuation of application No. 12/205,200, filed on Sep. 5, 2008, now abandoned.

(60) Provisional application No. 60/970,716, filed on Sep. 7, 2007.

(56) References Cited

FOREIGN PATENT DOCUMENTS

| WO | WO 99/00026 A1 | 1/1999 |
|---|---|---|
| WO | WO 99/21830 A1 | 5/1999 |
| WO | WO 00/19964 A2 | 4/2000 |
| WO | WO 2005/099680 A2 | 10/2005 |
| WO | WO 2006/021587 A1 | 3/2006 |
| WO | WO 2006/126214 A2 | 11/2006 |
| WO | WO 2007/092343 A2 | 8/2007 |

OTHER PUBLICATIONS

CDC, "Bloodstream Infections Among Patients Treated with Intravenous Epoprostenol or Intravenous Treprostinil for Pulmonary Hypertension—Seven Sites, United States 2003-2006," MMWR, vol. 56, No. 8 pp. 170-172 (Mar. 2007).
Chattaraj, Sarat C., "Treprostinil sodium Pharmacia," Curr. Opin. Invest. Drugs, 2002, 3:582-586.
Data, J., et al. "Intravenous Infusion of Prostacyclin Sodium in Man: Clinical Effects and Influence on Platelet Adenosine Diphosphate Sensitivity and Adenosine 3':5'-Cyclic Monophosphate Levels," Circulation, vol. 64, pp. 4-12 (1981).
De Jaegere, A.P.M.C. & van den Anker, J.N., "Endotracheal Instillation of Prostacyclin in Preterm Infants with Persistent Pulmonary Hypertension," Eur. Respir. J., vol. 12, pp. 932-934 (1998).
Debevere et al., "Effect of buffered acidulent systems on the survival of some food poisoning bacterial in medium acid media," Food Microbiology, 1988, 5(3):135-139.
Declaration of Keith M. Stolte in support of Sandoz Inc.'s Corrected Brief in Support of its Motion for Summary Judgment of Invalidity as to the claims of U.S. Pat. No. 7,999,007, in United therapeutics Corporation v. Sandoz Inc. et al., Civil Nos. 12-1617 and 13-316, Nov. 18, 2013, 2 pages.
Defendant Sandoz Inc.'s Corrected Brief in Support of its Motion for Summary Judgment of Invalidity as to the claims of U.S. Pat. No. 7,999,007, in United therapeutics Corporation v. Sandoz Inc. et al., Civil Nos. 12-1617 and 13-316, Nov. 19, 2013, 46 pages.
Defendant Sandoz Inc.'s Invalidity Contentions, filed Sep. 7, 2012, in United Therapeutics Corporation v. Sandoz, Inc., Civil Action No. 12-1617 (PGS)(LHG), 102 pages.
Denyer et al, Guide to Microbiological Control in Pharmaceuticals and Medical Devices, 2d Ed., pp. 24-50 (CRC Press 2006).
Flolan Package Insert (1999), 30 pages.
Flolan® (epoprostenol sodium) for Injection, prescribing information, Glaxo Smith Kline, 2002, 1-24.
Flolan® product label, GlaxoSmithKline, Research Triangle Park, North Carolina, Jan. 2008, 22 pgs.
Gomberg-Maitland et al., "Transition from Intravenous Epoprostenol to Intravenous Treprostinil in Pulmonary Hypertension," Am. J. Respir. Crit. Care Med., 2005, 172:1586-1589.
Henry, R., Clinical Chemistry Principles and Technics, 1974, 1585-1615.
Invalidity Contention Claim Charts for U.S. Pat. No. 7,999,007, filed Sep. 7, 2012, in United Therapeutics Corporation v. Sandoz, Inc., Civil Action No. 12-1617 (PGS)(LHG), 179 pages.
Kabara, Preservative-Free and Self-Preserving Cosmetics and Drugs, Principles and Practice, Chapters 1, 2 and 11 (1997)("Kabara"); Brannan, Cosmetic Microbiology—A Practical Handbook, pp. 47-48 (CRC Press 1997).
Kinner, et al, "Effect of Temperature, pH and Detergent on the Survival of Bacteria Associated with Shell Eggs," Poult. Sci., vol. 60, pp. 761-767 (1981).
Kiran et al., Current Treatment for Pulmonary Hypertension, The Internet Journal of Pulmonary Medicine, 2005, 4(2):1-6.
Kohler, F., Practical Handbook of Biochemistry and Molecular Biology, (Fasman, G., ed.) 530-550 (1989).
Laird, et al, "Survival of Listeria Monocytogenes in Egg Washwater," Int. J. Food Microbiol, vol. 12, pp. 115-122 (1991).
Li, P. & Zhao, Luwei, "Developing early formulations: Practice and perspective," International Journal of Pharmaceutics, vol. 341, pp. 1-19 (2007).
Lynch et al, "Bacterial Counts in Canine Duodenal Fluid After Exposure to Saline, Sodium Bicarbinate and Hypertonic Dextrose Solutions Used to Maintain Patency of Chronically Implanted Catheters," Laboratory Animals, Vo. 33, pp. 143-148 (1999).
McCormick et al., "Ocreotide Inhibits the Meal-induced Increases in the Portal Venous Pressure of Cirrhotic Patients with Protal Hypertension: A Double-blind, Placebo-controlled Study," Hepatology, 1992, 16(5):1180-1186.
McLaughlin et al., "Reduction in Pulmonary Vascular Resistance with Long-Term Epoprostenol (Prostacyclin) Therapy in Primary Pulmonary Hypertension," New England Journal of Medicine, Jan. 29, 1998, 338(5):273-277.
Mendonca et al., "Destruction of Gram-Negative Food-Borne Pathogens by High pH Involves Disruption of the Cytoplasmic Membrane," Applied and Environmental Microbiology, Nov. 1994, 60(11):4009-4014.
Mendonca, et al, "Destruction of Gram-Negative Food-Borne Pathogens by High pH Involves Disruption of the Cytoplasmic Membrane," Applied and Environmental Microbiology, vol. 60, No. 11, p. 4009-4014 (1994).
Mikhail, G., et al., "An Evaluation of Nebulized Prostacyclin in Patients with Primary and Secondary Pulmonary Hypertension," European Heart Journal, vol. 18, pp. 1499-1504 (1997).
Moncada, S., "Biology and Therapeutic Potential of Prostacyclin," Stroke, vol. 14, pp. 157-168 (1983).
Oudiz, "Micrococcus-Associated Central Venous Catheter Infection in Patients with Pulmonary Arterial Hypertension," Chest, vol. 126, No. 1, pp. 90-94 (Jul. 2004).
Pacios et al., "Influence on different vehicles on the pH of calcium hydroxide pastes," Journal of Oral Science, 2004, 46(2):107-111.
Pearson, et al, "Survival and Transport of Bacteria in Egg Washwater," "Appl. Environ. Microbiol.," vol. 53, pp. 2060-2065 (1987).
Phares et al., "Stability and preservative effectiveness of treprostinil sodium after dilution in common intravenous diluents," Am. J. Health-Syst. Phram., May 1, 2003, 60:916-922.
Remington, The Science and Practice of Pharmacy, $21^{st}$ Edition, 2006, 231-265, 802-849, 1018-1036, 1318-1378, 1958-1967, 2290-2302.
Remodulin Package Insert (2006), 14 pages.
Sørenson, S.P.L., Ergeb. Physiol. vol. 12, 394-532 (1912).
Southam, et al, "Survival and Growth of Yersinia Enterocolitica in Egg Washwater," J. Food Prot., vol. 50, pp. 103-107 (1987).
Tilley, F.W., "The Influence of Changes in Concentration of Sodium Hydroxide Upon its Bactericidal Activity," J. Bacteriol., 1946, 51(6):779-785.
Toro, G. & Ackermann, P. G., Practical Clinical Chemistry, at p. 741 (1975).
Whittle, B. & Moncada, S., "Platelet Actions of Stable Carbocyclic Analogues of Prostacyclin," Circulation, vol. 72, pp. 1219-1225 (1985).
McLaughlin et al., "Efficacy and Safety of Treprostinil: An Epoprostenol Analog for Primary Pulmonary Hypertension," Journal of Cardiovascular Pharmacology, 2003, 41:293-299.

* cited by examiner

BUFFER SOLUTIONS HAVING SELECTIVE BACTERICIDAL ACTIVITY AGAINST GRAM NEGATIVE BACTERIA AND METHODS OF USING SAME

CROSS REFERENCE TO RELATED APPLICATIONS

This application is a Continuation of U.S. patent application Ser. No. 13/912,753, filed Jun. 7, 2013, which is a Continuation of U.S. patent application Ser. No. 13/022,005, filed Feb. 7, 2011, which is a Continuation of U.S. patent application Ser. No. 12/276,707, filed Nov. 24, 2008, now U.S. Pat. No. 7,999,007, which is a Continuation of U.S. patent application Ser. No. 12/205,200, filed Sep. 5, 2008, which claims priority to U.S. Patent Application 60/970,716, filed Sep. 7, 2008, the entire contents of which are incorporated herein by reference.

FIELD OF THE INVENTION

The present invention relates generally to the field of buffer solutions having bacteriostatic and/or bactericidal activity. More specifically, the present invention relates to buffer solutions that have bactericidal activity preferentially against gram negative bacteria.

BACKGROUND OF THE INVENTION

The use of buffers to maintain a pH and solubilize or dilute active pharmaceutical agents ("APIs") before administration (e.g., by injection) is routine. Many buffers, however, contain components that maintain a neutral pH and foster microbial growth, which can lead to sepsis and other undesirable infection-related complications.

Gram negative bacteria are a particularly troublesome class of microbes, as they are commonplace in the hospital environments and difficult to eradicate and/or control. Infections with this class of bacteria tend to have higher morbidity/mortality rates when a patient becomes septic, in part, because gram negative bacteria are especially difficult organisms to treat. Also, gram negative bacteria are associated with water contamination which can occur with chronic indwelling catheters such as used with intravenous administration. Hence, there is a need for buffer systems that have anticidal activity with specificity to gram negative bacteria.

SUMMARY OF THE INVENTION

In one embodiment of the present invention, a method of selectively killing gram negative bacteria and inhibiting the growth of gram positive bacteria in a pharmaceutical preparation comprising an active agent is provided, the method comprising supplying the active agent with a buffer having a pH of greater than about 10 or less than about 4.5 and a low buffer capacity, wherein the pharmaceutical preparation does not comprise epoprostenol sodium as the sole active agent. In addition to bacteria, the buffer may further inhibit the growth of fungus, mold, or both. Preferably, the buffer has a pH between about 10 to about 12, more preferably a pH between about 10.2 to about 10.8. In other embodiments, the buffer has a pH between about 3 and 4.5, more preferably a pH between about 3.5 and 4.5.

The buffer may comprise glycine; and in a specific embodiment, the buffer is sterile diluent for FLOLAN®, namely a buffer comprising glycine and sodium hydroxide, added to adjust the pH to 10.2 to 10.8. The active agent may be any active pharmaceutical agent that requires solution or dilution with a buffer and may be injected (e.g., intravenously). The active agent may be treprostinil sodium (sometimes referred to herein as treprostinil), preferably supplied at a concentration between about 0.004 mg/mL to about 0.13 mg/mL treprostinil sodium.

The buffer may comprise sorbic acid or citric acid or any other weak acid that is pharmaceutically acceptable for parenteral use. The pH can be adjusted with hydrochloric acid or sodium hydroxide to attain a final pH between 3 and 4.5. The active agent may be any active pharmaceutical agent that requires solution or dilution with a buffer and may be injected (e.g., intravenously).

In another embodiment of the invention, a method of reducing the occurrence of blood stream infections in a mammal being treated with an active agent is provided, the method comprising administering to the mammal the active agent with a buffer having a pH of greater than about 10 or less than about 4.5 and a low buffer capacity, wherein the active agent is not epoprostenol sodium, and wherein the administration reduces the gram negative bacteria and inhibits the growth of gram positive bacteria. In some cases, the human subject may suffer from pulmonary arterial hypertension.

Preferably, the buffer has a pH between about 10 to about 12, more preferably a pH between about 10.2 to about 10.8 and a low buffer capacity. Alternatively, the buffer has a pH preferably between about 3 to about 4.5, more preferably a pH between about 3.5 to about 4.5 and a low buffer capacity. The buffer may comprise glycine; and in a specific embodiment, the buffer is sterile diluent for FLOLAN®. The active agent may be any active pharmaceutical agent that requires solution or dilution with a buffer and may be injected (e.g., intravenously). The active agent may be treprostinil sodium, preferably supplied at a concentration between about 0.004 mg/mL to about 0.13 mg/mL treprostinil. Selection of the buffer will depend on the desired pH. While the buffer components should have a pKa close to the desired pH, the buffer capacity should be low to avoid pH changes in the blood upon infusion. A preferred buffer capacity for such buffers is 0.01 and less.

The legend for FIGS. 6-15 is as follows:
(open circles): FLOLAN® in Sterile Diluent for FLOLAN®
(closed circles): Treprostinil in Sterile Diluent for FLOLAN®
(open squares): Treprostinil in sterile water for injection
(closed squares): Treprostinil in bacteriostatic water for injection (open diamonds): Treprostinil in normal (0.9%) saline
(closed diamonds): Treprostinil in bacteriostatic normal saline
(open triangle): Treprostinil in 5% dextrose in water for injection (D5W).

Figure 7:
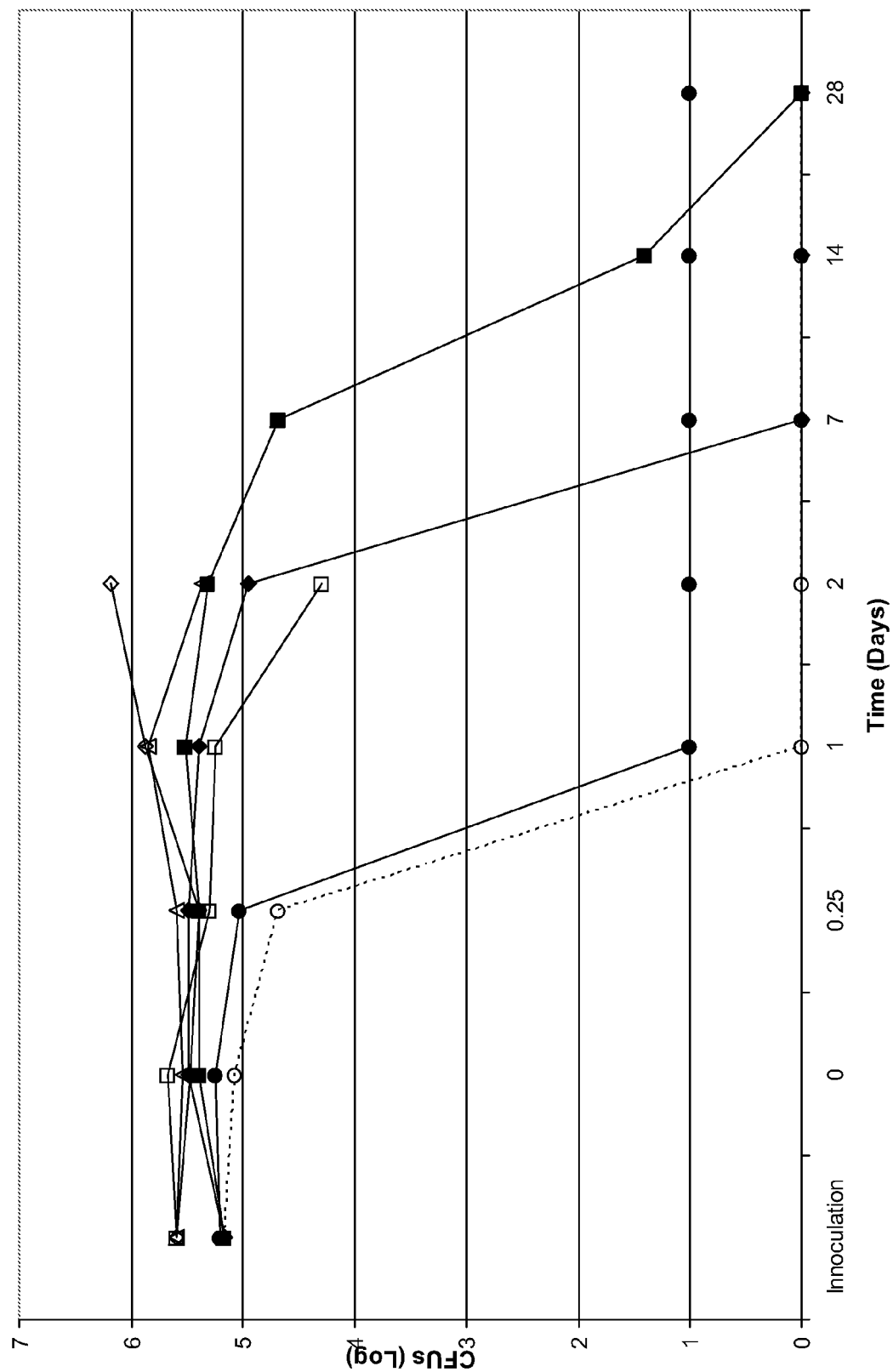

FIG. 7 is a graph showing the antimicrobial activity (CFU) over time (days) of various buffer systems against *Escherichia coli*, a gram negative bacterium, in a pharmaceutical preparation comprising 0.004 mg/mL treprostinil. Values for ≤Log 1 (treprostinil in sterile diluent) recorded as Log 1.

Figure 8:
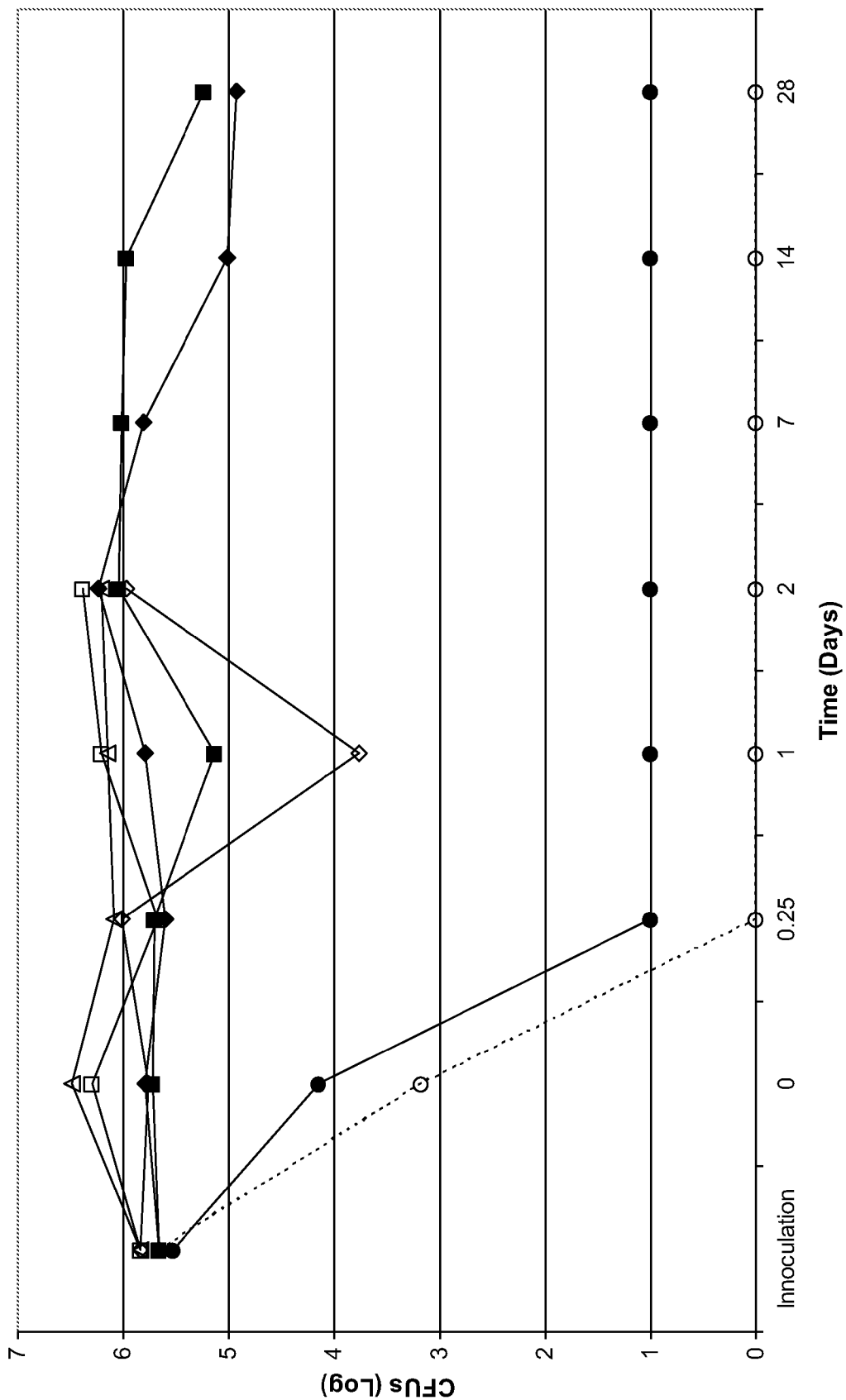
Figure 9:
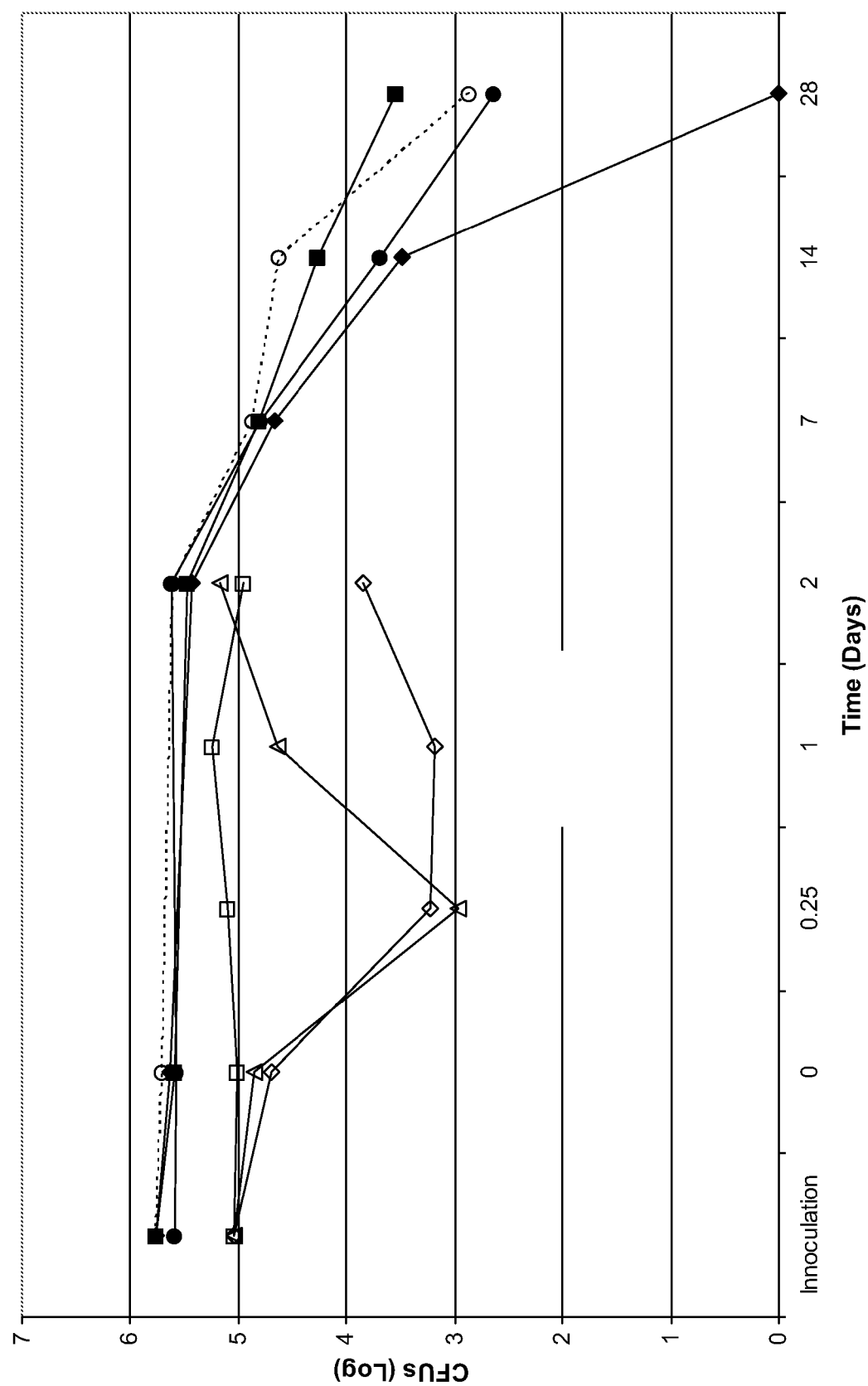

FIG. 8 is a graph showing the antimicrobial activity (CFU) over time (days) of various buffer systems against *Pseudomonas aeruginosa*, a gram negative bacterium, in a pharmaceutical preparation comprising 0.004 mg/mL treprostinil. Values≤Log 1 (treprostinil in sterile diluent) or ≥6.48 (treprostinil in D5W) are recorded as Log 1 and Log 6.48, respectively FIG. 9 is a graph showing the antimicrobial activity (CFU) over time (days) of various buffer systems against *Candida albicans*, a fungus, in a pharmaceutical preparation comprising 0.004 mg/mL treprostinil.

Figure 10:
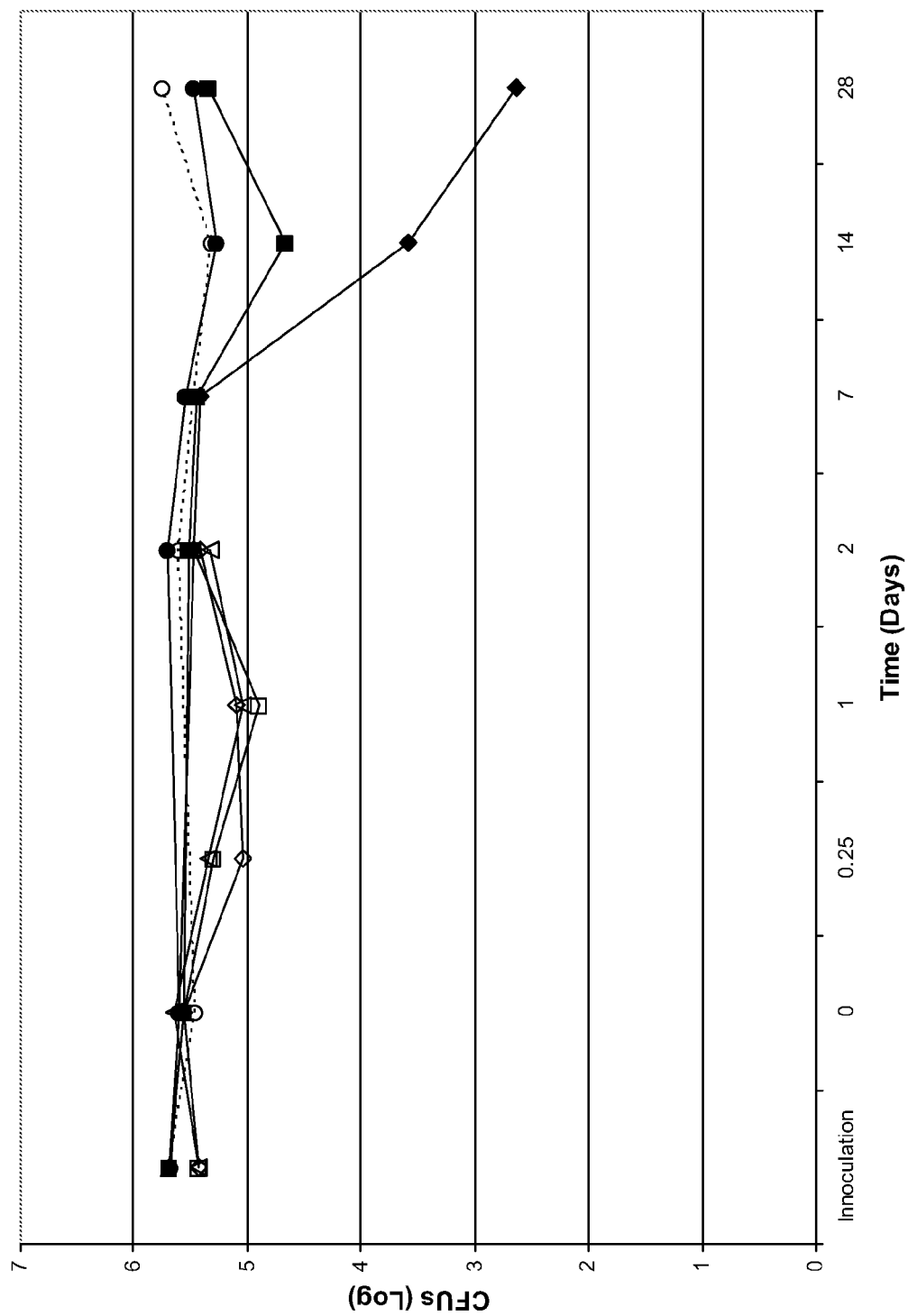

FIG. 10 is a graph showing the antimicrobial activity (CFU) over time (days) of various buffer systems against *Aspergillus niger*, a mold, in a pharmaceutical preparation comprising 0.004 mg/mL treprostinil.

Figure 11:
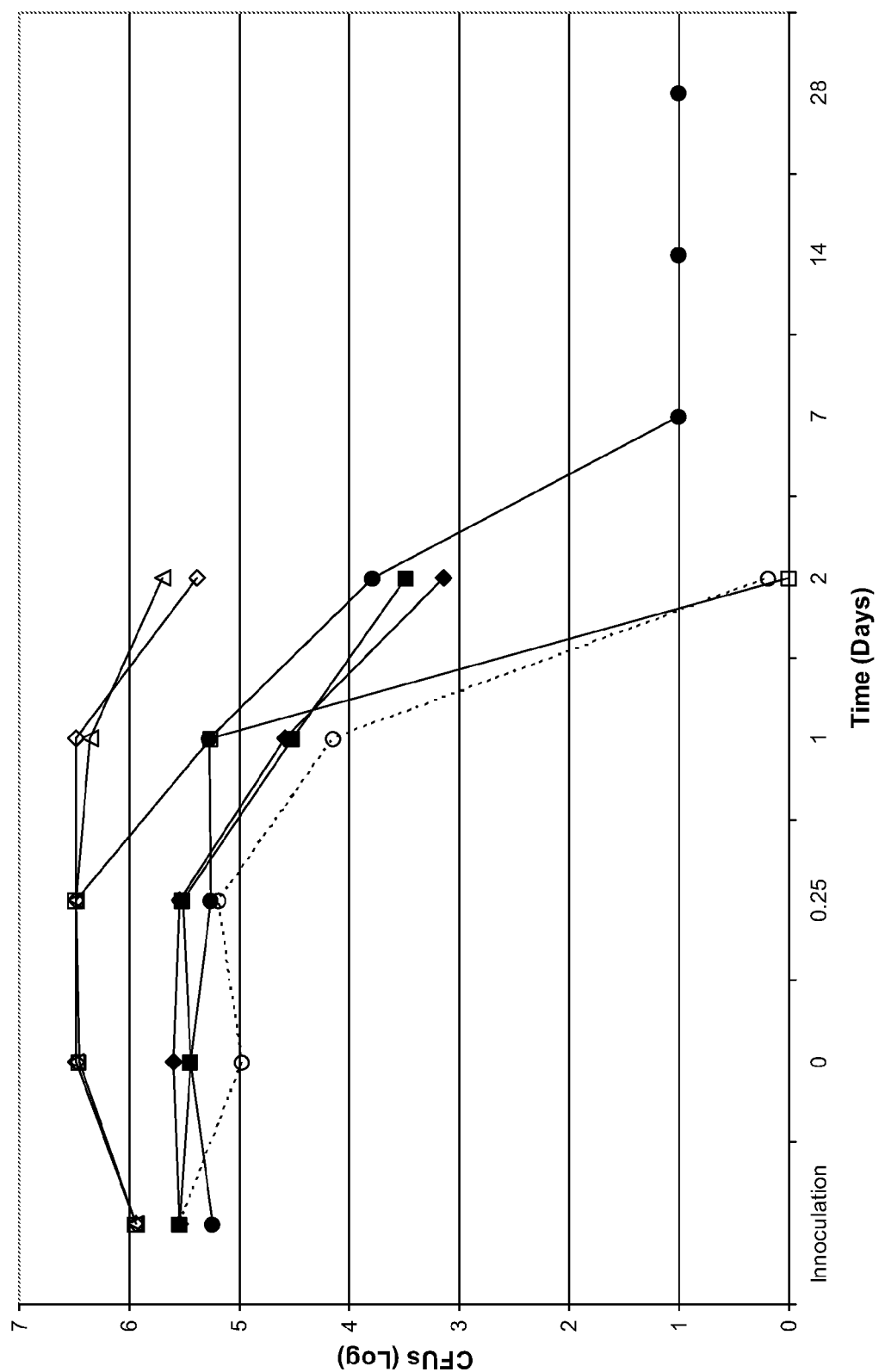

FIG. 11 is a graph showing the antimicrobial activity (CFU) over time (days) of various buffer systems against *Staphylococcus aureus*, a gram positive bacterium, in a pharmaceutical preparation comprising 0.13 mg/mL treprostinil. Values for ≤Log 1 (treprostinil in sterile diluent) or ≥Log 6.48 (treprostinil in WFI, NS, D5W) are recorded as Log 1 and Log 6.48, respectively.

Figure 12:
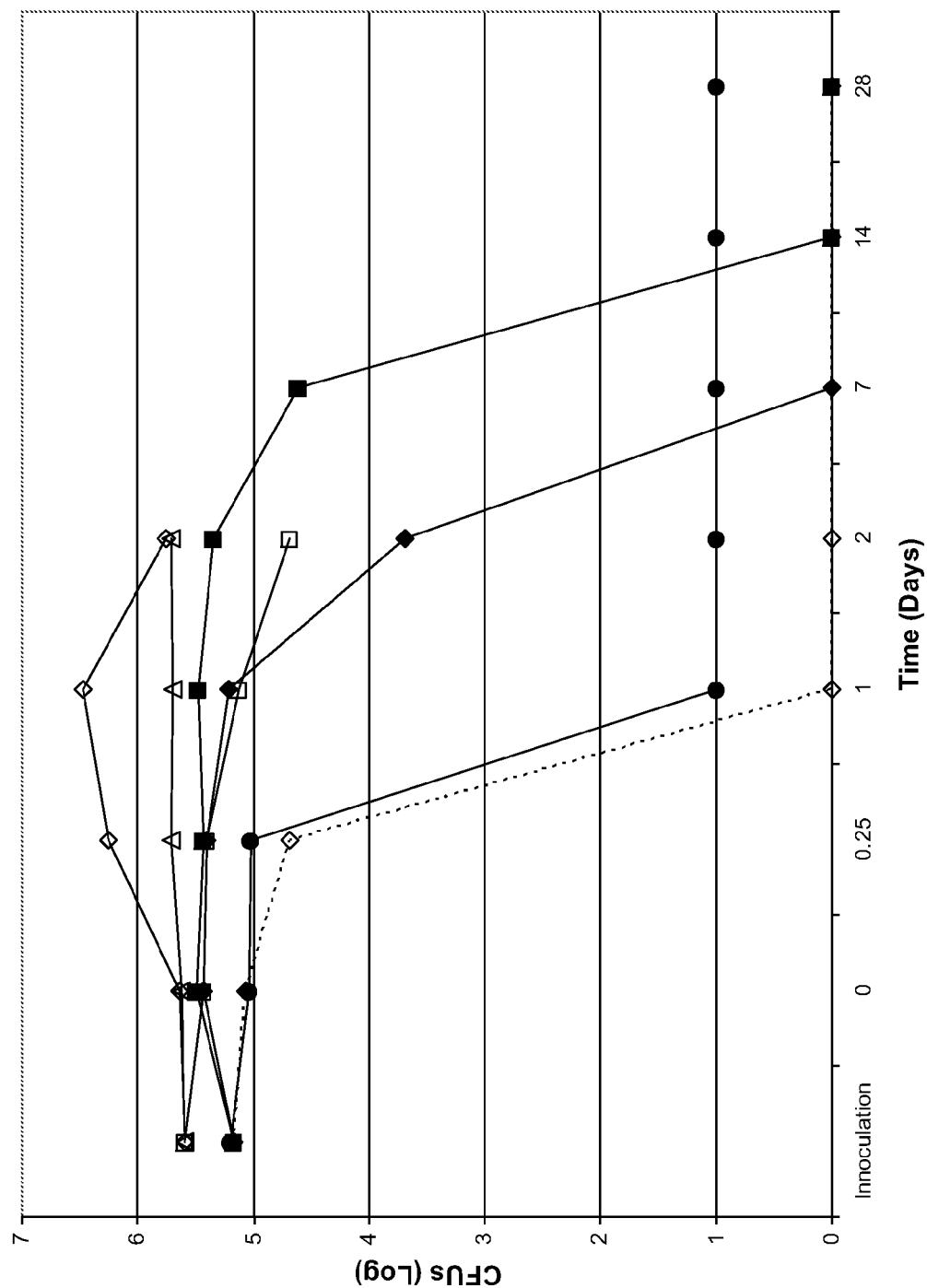

FIG. 12 is a graph showing the antimicrobial activity (CFU) over time (days) of various buffer systems against *Escherichia coli*, a gram negative bacterium, in a pharmaceutical preparation comprising 0.13 mg/mL treprostinil. Values for ≤Log 1 (treprostinil in sterile diluent) or ≥Log 6.48 (treprostinil in NS) are recorded as Log 1 and Log 6.48, respectively.

Figure 13:
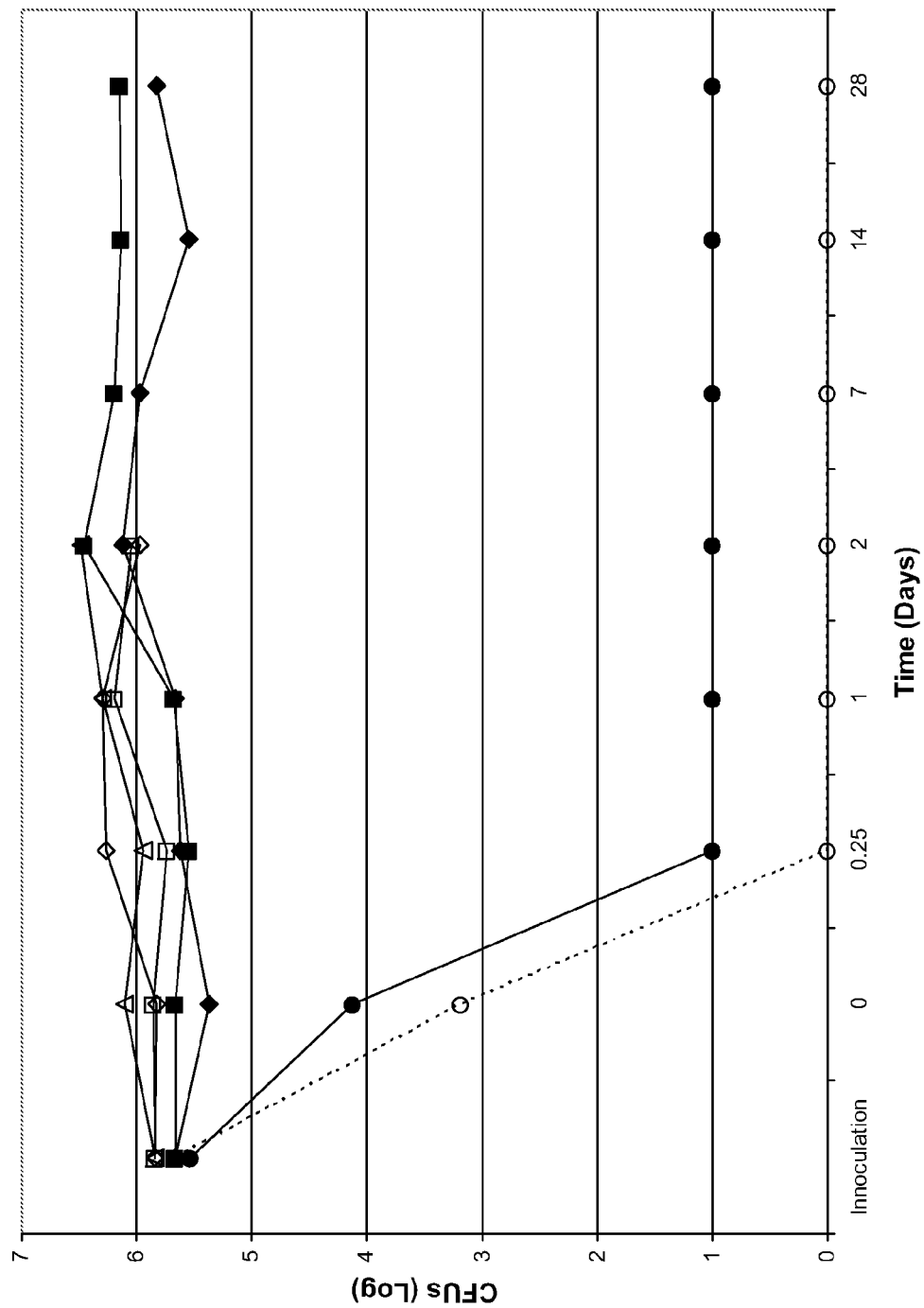

FIG. 13 is a graph showing the antimicrobial activity (CFU) over time (days) of various buffer systems against *Pseudomonas aeruginosa*, a gram negative bacterium, in a pharmaceutical preparation comprising 0.13 mg/mL treprostinil. Values for ≤Log 1 (treprostinil in sterile diluent) recorded as Log 1.

Figure 14:
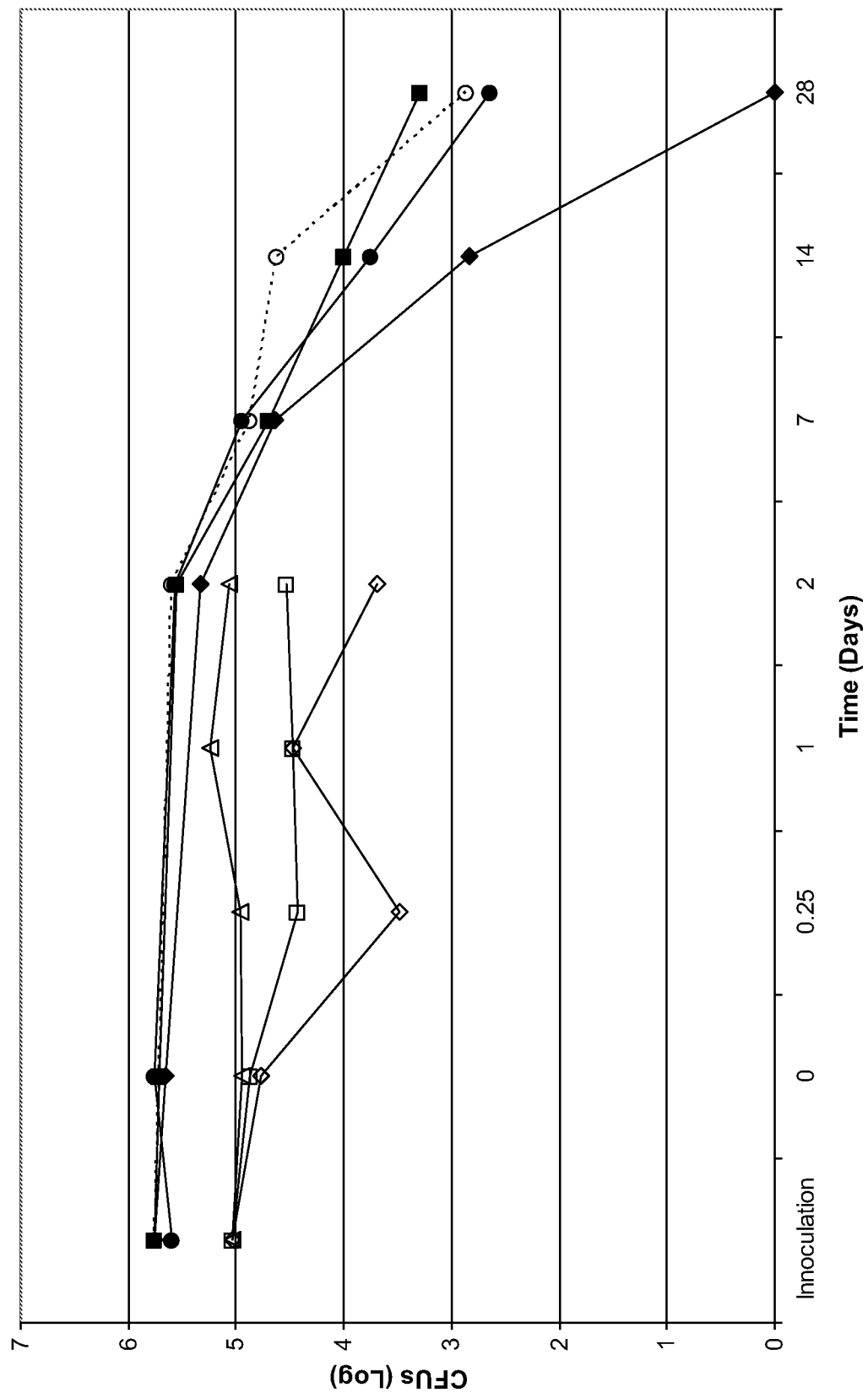

FIG. 14 is a graph showing the antimicrobial activity (CFU) over time (days) of various buffer systems against *Candida albicans*, a fungus, in a pharmaceutical preparation comprising 0.13 mg/mL treprostinil. Value≥Log 3.48 at time 0.25 hours for treprostinil in NS recorded as Log 3.48.

Figure 15:
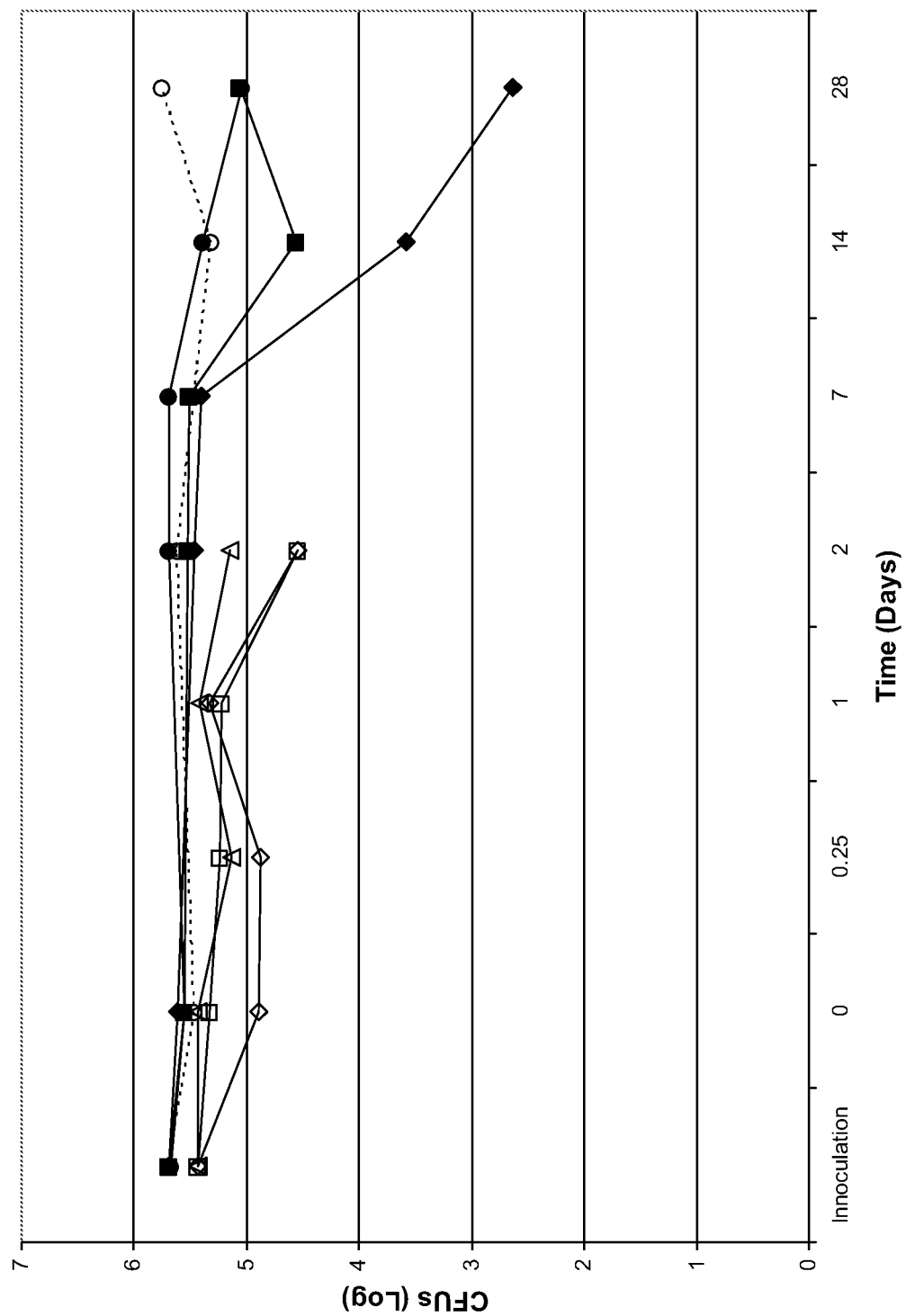

FIG. 15 is a graph showing the antimicrobial activity (CFU) over time (days) of various buffer systems against *Aspergillus niger*, a mold, in a pharmaceutical preparation comprising 0.13 mg/mL treprostinil.

DETAILED DESCRIPTION OF THE PREFERRED EMBODIMENTS

The present invention is directed to the use of buffer systems to maintain a specific pH range as anticidal agents in pharmaceutical preparations. The term "buffer" as used herein refers to any solution with a controlled pH that may serve to dissolve a solid (e.g., lyophilized) pharmaceutical or as a diluent to dilute a liquid pharmaceutical. According to the invention, the buffers described herein maintain a pH that exhibits bacteriostatic activity toward most, if not all, microbes, including bacteria, molds and fungi and further exhibit bactericidal activity toward gram negative bacteria. Examples of gram negative bacteria include *Escherichia coli, Pseudomonas aeruginosa, Salmonella, Moraxella, Helicobacter, Stenotrophomonas, Bdellovibrio, Legionella, Neisseria gonorrhoeae*, and *Neisseria meningitidis*. Gram negative bacteria are a common source of infection in hospital environments and therefore buffers that maintain a pH above 10 or less than about 4.5 with low buffer capacity have bactericidal activity specific for gram negative bacteria are desirable. By way of example, gram positive bacteria include *Staphylococcus aureus Bacillus, Listeria, Staphylococcus, Streptococcus, Enterococcus*, and *Clostridium*.

"Bacteriostatic" is defined as the ability to retard or prevent the expansion of a microbe that might be present, or become present, in the buffer solution. In other words, "bacteriostatic" activity does not include bactericidal activity, which is defined herein as activity that kills a microbe that might be present, or become present, in the buffer. Microbes are broadly defined herein to include unicellular organisms, such as, for example, bacteria, molds, and fungi.

The present inventors have learned that buffers having high pH (>10) or low pH (<4.5) have bactericidal activity specific for gram negative bacteria and bacteriostatic activity toward gram positive bacteria and other microbes. Without being held to or bound by theory, it is currently believed that differences in the biochemistry, perhaps cell wall biochemistry, between gram negative and gram positive bacteria may account for their differential sensitivity toward high pH buffers. In the context of the present invention, "high" pH is a pH value of about 9 to about 12, preferably about 10 to about 12. In a preferred embodiment of the invention, buffers have a pH of about 10.2 to about 10.8 or about 3.5 to about 4.5.

In addition to high pH, the present inventors have learned the buffers comprising glycine are particularly advantageous. In such embodiments, glycine is present at a concentration (w/w) of about 30% to about 80%, preferably about 45% to about 65%, and most preferably, about 50% to about 60%. The term "about" is used herein in recognition of the inherent inaccuracies in calculations and measurements in the art and to include nominal and accepted variations "about" the recited numeral.

In addition to glycine, buffers as described herein may comprise any other buffer system, including those known in the art, that can maintain a pH in the ranges stated herein.

In a specific embodiment of the present invention, the diluent for FLOLAN® (epoprostenol sodium) employs glycine as a buffer component. As will be described in greater detail below, the diluent for FLOLAN® was unexpectedly discovered to have specific anticidal activity toward gram negative bacteria and bacteriostatic activity toward remainder microbes. The diluent for FLOLAN® comprises 50 mL of 94 mg glycine, 73.3 mg sodium chloride, and sodium hydroxide, added to adjust the pH to 10.2 to 10.8. (About 44% NaCl in glycine.)

The buffers as described herein may be suitable for any active pharmaceutical ingredient ("API") that is stable at high pH and provided that the chemical properties of the API do not substantially drop the pH of the buffer below, for example, about 10. Hence, the following examples notwithstanding, the present invention should not be limited to any one or any one class of API nor, for that matter, a limited range of concentrations. Further, the novel and unexpected anticidal properties of the buffers may be especially suited for medicaments that are administered by injection. Indeed, in one embodiment of the invention, it is anticipated that use of the high and low pH buffers as described herein can reduce the occurrence of blood stream infections in a mammal being treated with an active agent. It should be noted, however, that the present invention is not limited to medicaments that are prescribed for injection (including intravenous injection), but any medicament that requires solution and/or dilution (e.g., for oral administration).

In a specific embodiment of the present invention, the buffer systems described are used with treprostinil sodium. More specifically, as will be next disclosed by way of examples, the diluent for FLOLAN® is used to buffer treprostinil sodium.

Examples

A compatibility study of treprostinil with a 100-mL CADD delivery device was performed. More specifically, the compatibility and stability of treprostinil diluted with bacteriostatic water for injection ("BWFI") or bacteriostatic normal saline ("BNS"), both of which are preserved with parabens, was determined. The sample solutions were prepared at 0.004 mg/mL and 0.13 mg/mL treprostinil, which comprises the entire range of concentrations at which treprostinil might be prescribed, and placed in a SIMS Deltec, Inc. CADD-Legacy™ (Model 6400) Pump delivery device that was pumped continuously over a period of 52 hours while stored at 40° C. and ambient relative humidity ("RH").

At specified time points (e.g., $T_0$, initial, 24 hours, and 52 hours), samples were collected from the distal end of the tube after pump and characterized for appearance, pH, and concentration of treprostinil. Furthermore, the solutions were subjected to antimicrobial effectiveness testing ("AET") over a similar time period of about 2 days. A similar experimental procedure was followed for Flolan reconstituted solutions. However, sterility and AET testing were performed on FLOLAN® after only 8 hours at room temperature on account of the medicament's limited stability in solution.

Figure 1A:
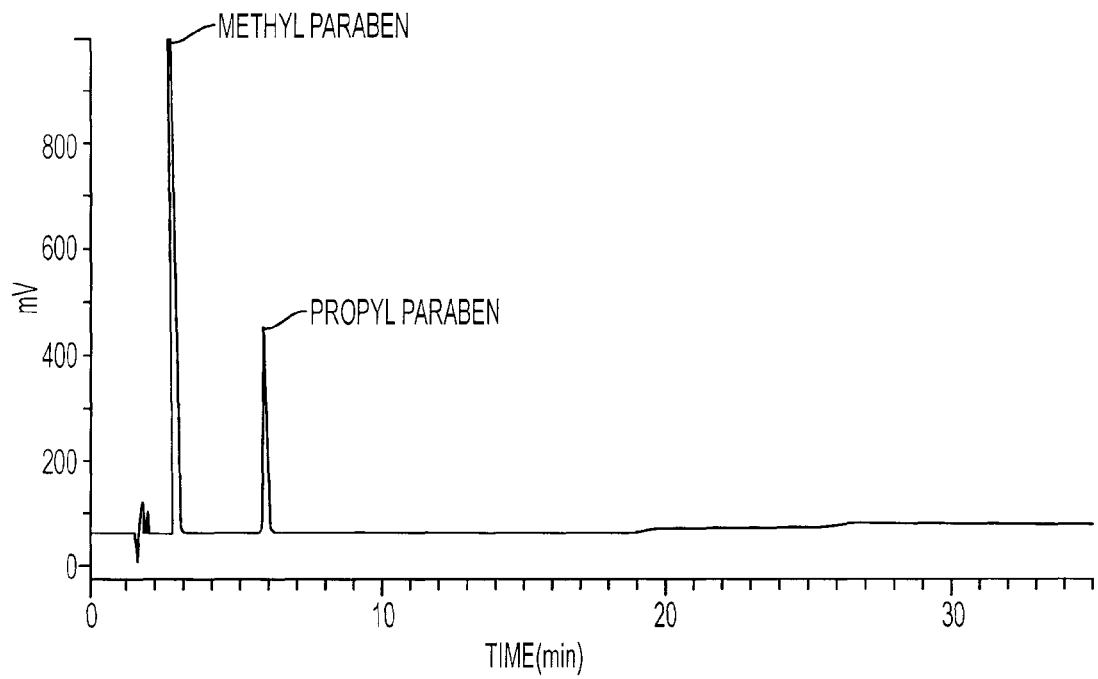
FIGS. 1A and 1B are chromatograms of a "blank" injection of BWFI (A) and treprostinil diluted with BWFI (B).
Figure 1B:
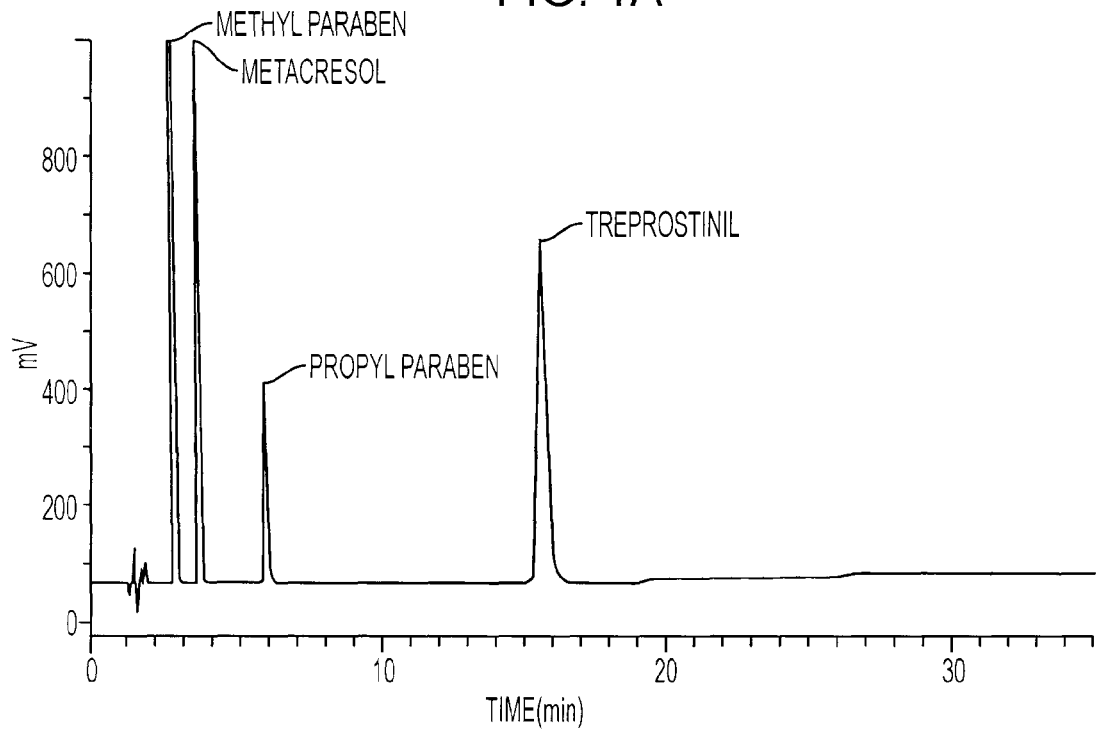
Figure 2A:
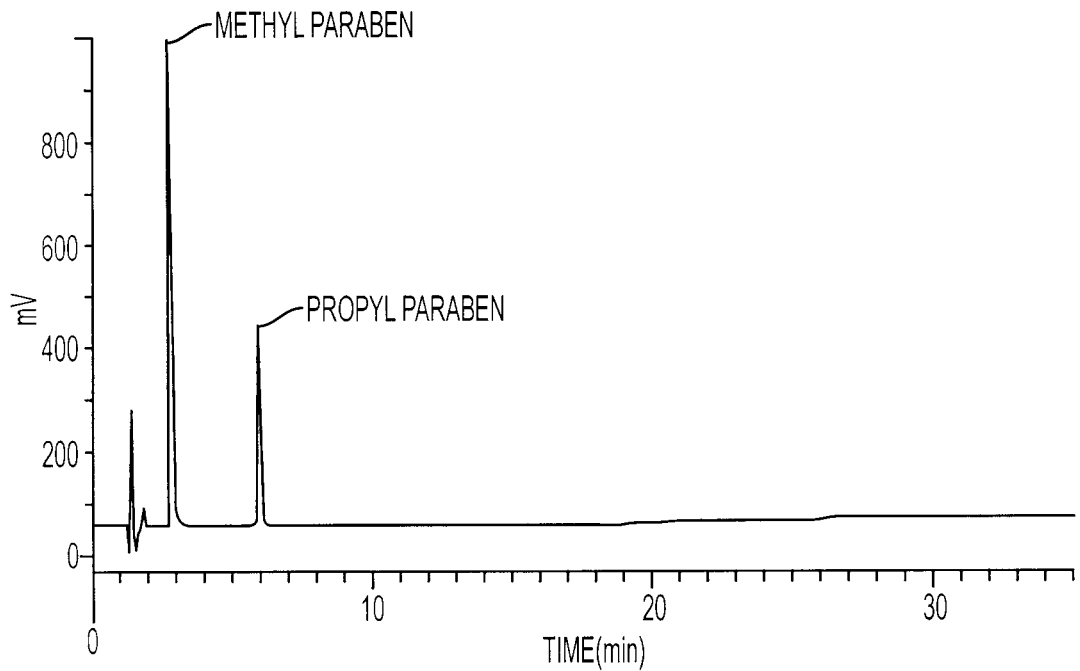
FIGS. 2A and 2B are chromatograms of a "blank" injection of BNS (A) and treprostinil diluted with BNS (B).
Figure 2B:
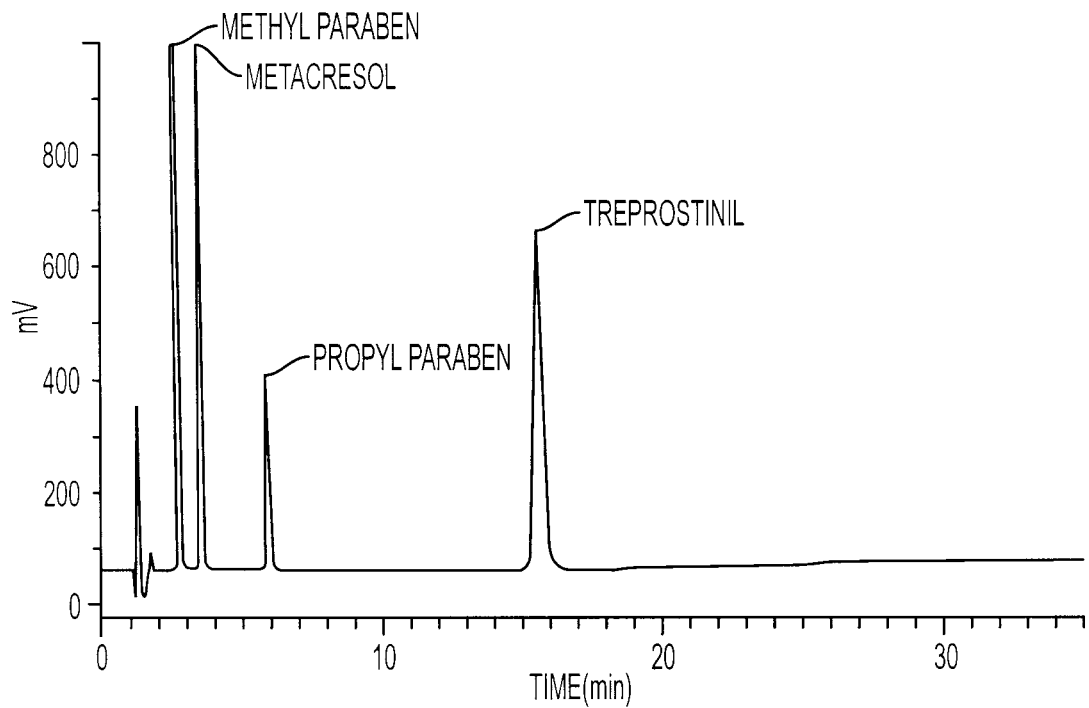
Figure 3A:
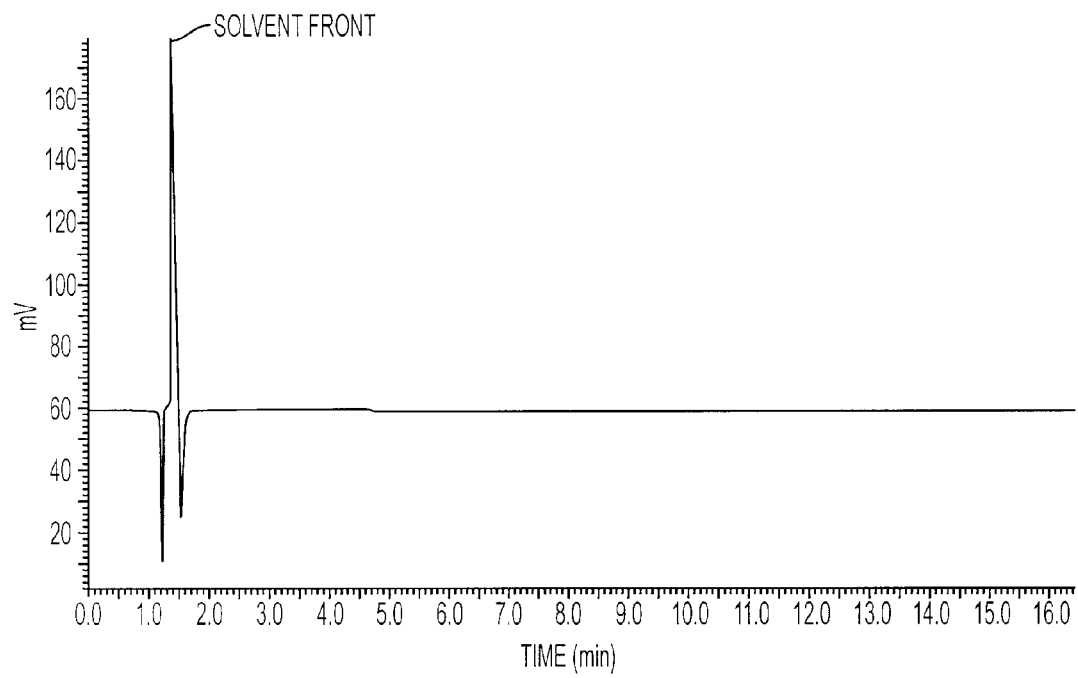
FIGS. 3A and 3B are chromatograms of Sterile Diluent for FLOLAN® (A) and treprostinil diluted with same (B).
Figure 3B:
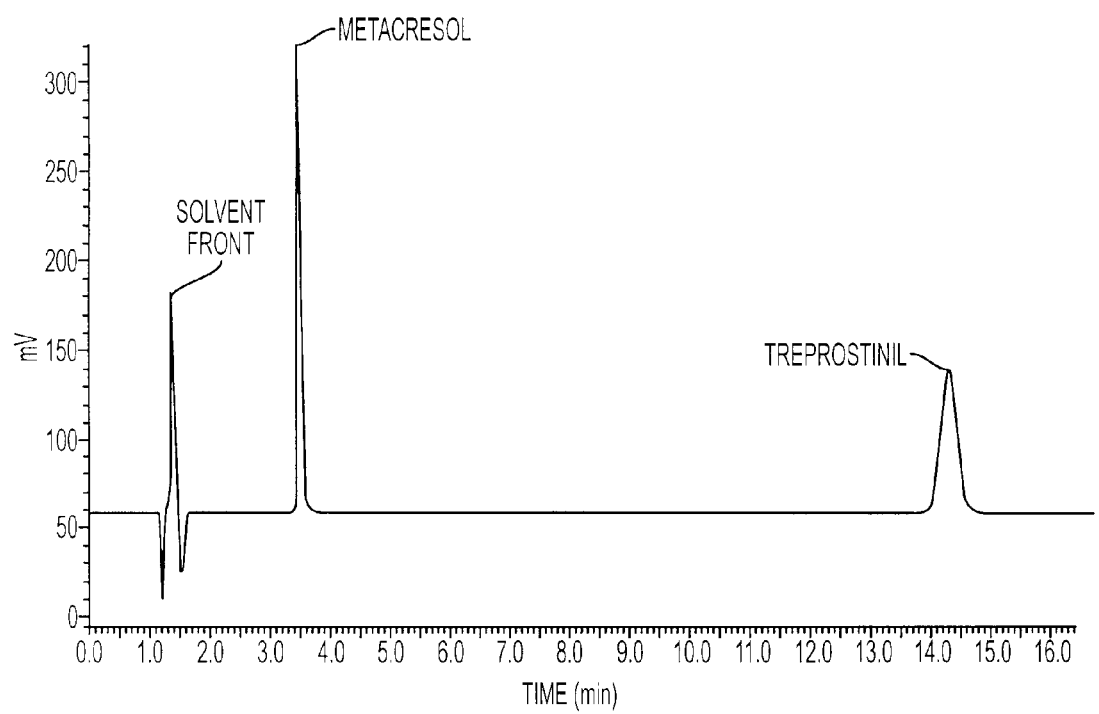

The stability of treprostinil was monitored by a fully validated stability indicating HPLC assay. In order to ascertain whether parabens—present in the "bacteriostatic" solutions—would cause interference in the chromatography with treprostinil, a preliminary experiment confirmed that the paraben "peaks" did not interfere with the treprostinil "peak" Or any impurity "peak." Solutions of BWFI and BNS, and treprostinil diluted in BWFI and BNS were analyzed using HPLC. FIGS. 1 and 2 shows that the paraben peaks from either methyl- or ethyl-paraben did not interfere (e.g., overlap) with the peak for treprostinil. There was also no chromatographic interference of treprostinil with Sterile Diluent for FLOLAN® (FIG. 3).

A low-level linearity study was also performed to cover the expected concentration range of treprostinil in the dilute solutions. Five solutions of treprostinil were prepared at 0.002, 0.01, 0.05, 0.1, and 0.15 mg/mL (diluted from the 1.0 mg/mL standard solution) and each solution was injected in duplicate. The intention was to prove linearity between the detector response and treprostinil concentration within the diluted concentration range in order to use a single-point standard at 0.1 mg/mL during the analysis. The detector response for treprostinil was determined to be linear from 0.002 to 0.15 mg/mL. The correlation coefficient (r) for the experiment was 0.999995, meeting the requirement of at least 0.999.

Solutions of 0.004 mg/mL treprostinil in BWFI, BNS, or Sterile Diluent for FLOLAN® were prepared from the 1.0 mg/mL strength of Remodulin. Solutions of 0.13 mg/mL treprostinil in BWFI and in BNS were prepared from the 10 mg/mL strength of Remodulin. Vials of FLOLAN® were reconstituted with 5 mL of Sterile Diluent for FLOLAN® using the procedure outlined in the package insert.

A portion (approximately 2 mL) of each of the four solutions was removed for $T_0$ analysis. The remaining solution was loaded into each of four separate SIMS Deltec, Inc. 100-mL Medication Cassette™ Reservoirs. The cassettes and tubing were attached to the CADD-Legacy™ 1 Pump following the manufacturers instructions. The four cassette/CADD pump sets were placed in a 40° C./Ambient RH chamber. A needle at the end of the tubing was placed into a sealed HPLC vial (with needle vent). The flow on the pump was set to 40 mL/24 hours and started. The solution from each pump was collected into separate HPLC vials (for about an hour) for testing at the "Initial" interval. The needle was then transferred to a sealed waste container (with needle vent). At 24 and 52 hours, the solution was collected again into a new, sealed HPLC vial for testing.

The solutions collected at $T_0$, initial, 24 hours, and 52 hours were analyzed for physical appearance, pH, and assayed by HPLC for treprostinil. Tables 1 and 2 summarize the results for treprostinil diluted with BWFI and BNS, respectively. The appearance of all solutions was clear and colorless, free from visible particulate matter. Hence, the results show no compatibility problems for the treprostinil solution in BWFI or BNS at either concentration.

TABLE 1

Chemical testing results for treprostinil in BWFI

| Concentration (mg/mL) | Prep- aration Testing | | Testing Interval | | | |
|---|---|---|---|---|---|---|
| | | | $T_0$ | $T_{initial}$ | 24 hours | 52 hours |
| 0.004 | Treprostinil | 1 | 104.1 | 99.5 | 100.8 | 99.6 |
| | Assay | 2 | 100.6 | 100.6 | 101.1 | 101.0 |
| | (% LC) | Average | 102.4 | 100.0 | 101.0 | 100.3 |
| | pH | NA | 6.7 | 6.8 | 6.8 | 6.8 |
| 0.13 | Treprostinil | 1 | 100.1 | 99.6 | 100.4 | 101.2 |
| | Assay | 2 | 100.0 | 99.8 | 100.5 | 100.9 |
| | (% LC) | Average | 100.0 | 99.7 | 100.5 | 101.0 |
| | pH | NA | 6.7 | 6.9 | 6.8 | 7.0 |

LC: Label claim

TABLE 2

Chemical testing results for treprostinil in BNS

| Concentration (mg/mL) | Prep- aration Testing | | Testing Interval | | | |
|---|---|---|---|---|---|---|
| | | | $T_0$ | $T_{initial}$ | 24 hours | 52 hours |
| 0.004 | Treprostinil | 1 | 97.8 | 94.8 | 96.7 | 99.9 |
| | Assay | 2 | 102.9 | 94.0 | 97.9 | 102.3 |
| | (% LC) | Average | 100.4 | 94.4 | 97.3 | 101.1 |
| | pH | NA | 6.4 | 6.6 | 6.6 | 6.6 |
| 0.13 | Treprostinil | 1 | 100.1 | 96.3 | 99.8 | 100.3 |
| | Assay | 2 | 100.5 | 96.0 | 99.7 | 100.2 |
| | (% LC) | Average | 100.3 | 96.1 | 99.7 | 100.2 |
| | pH | NA | 6.3 | 6.7 | 6.7 | 6.5 |

LC: Label claim

Figure 4A:
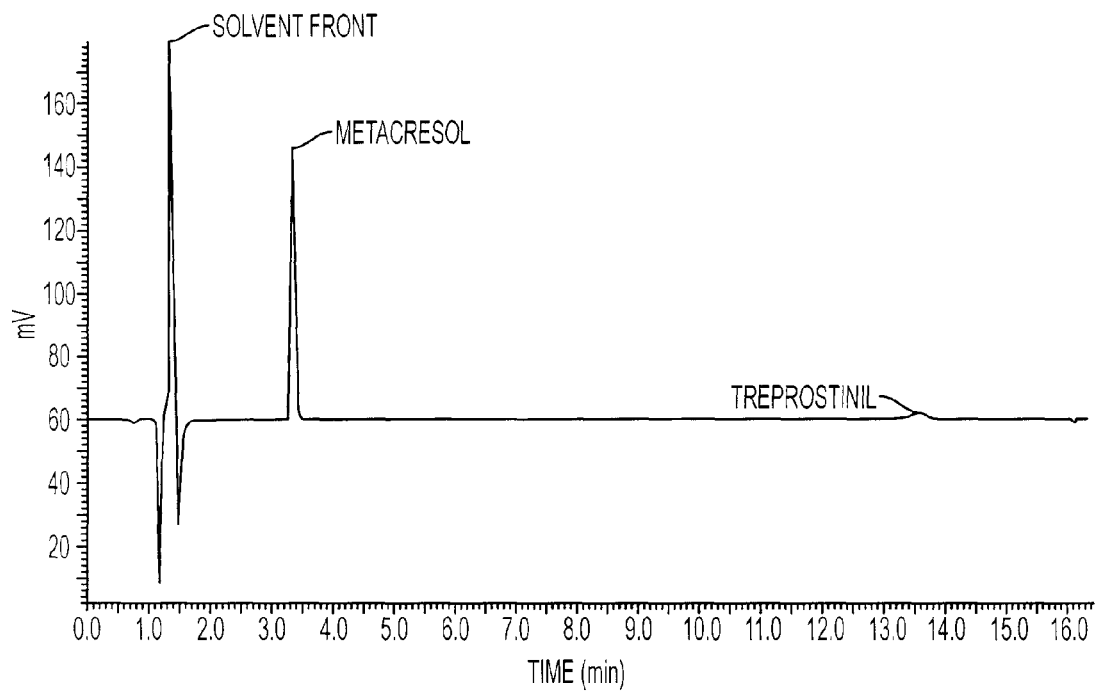
FIGS. 4A and 4B are chromatograms of 0.004 mg/mL treprostinil in Sterile Diluent for FLOLAN® at $T_0$ (A) and $T_{initial}$ (B).
Figure 4B:
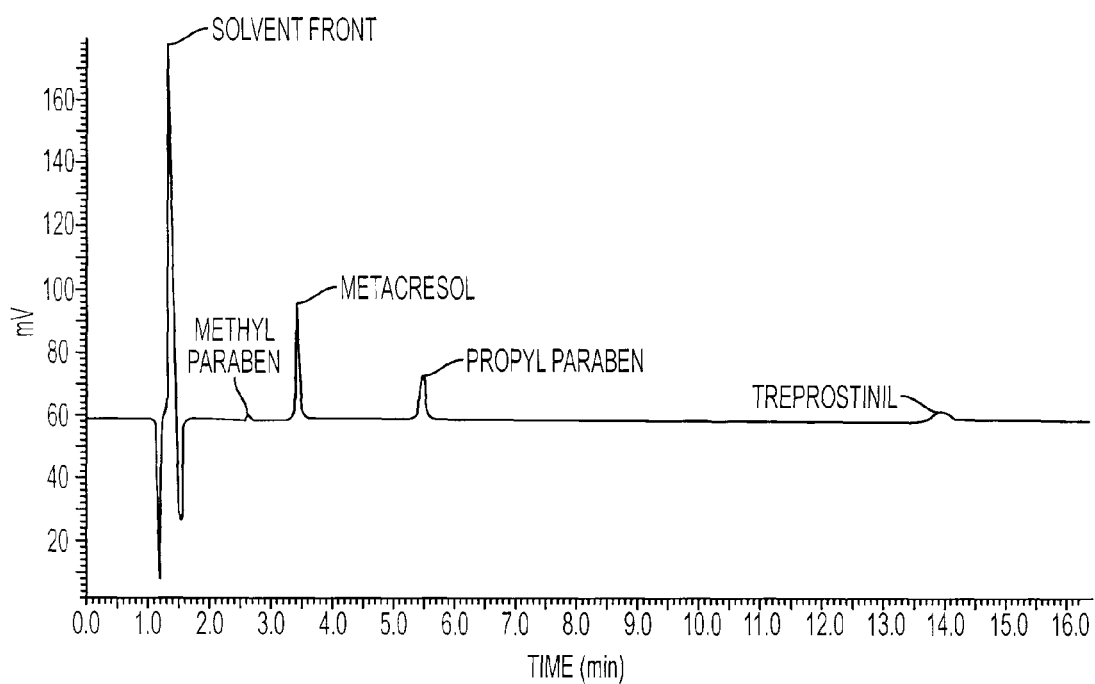
Figure 5A:
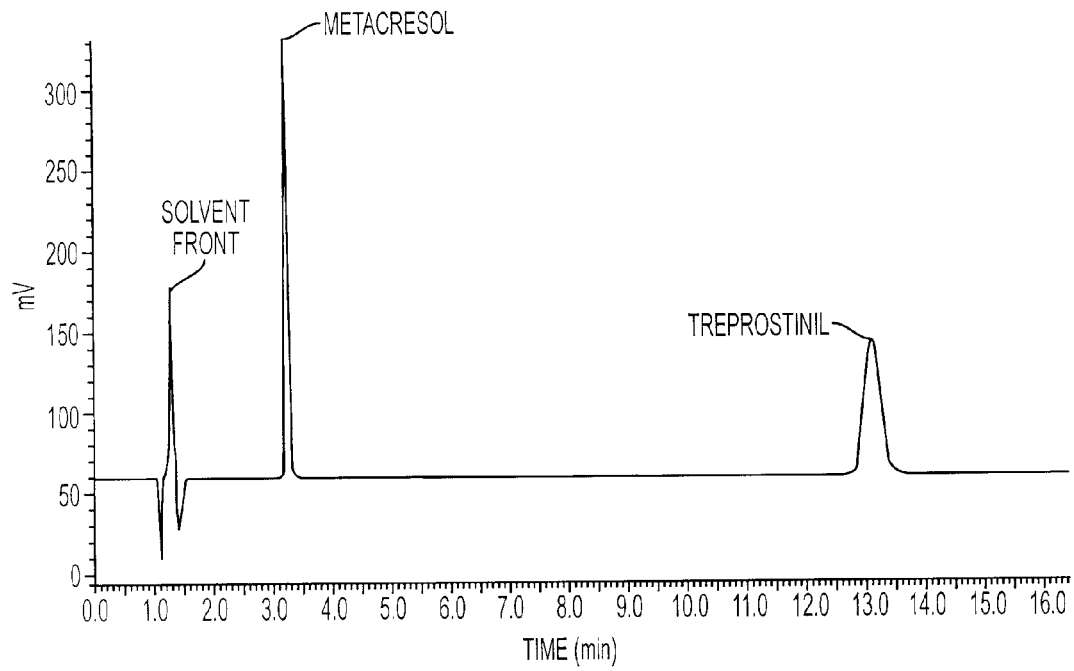
FIGS. 5A and 5B are chromatograms of 0.13 mg/mL treprostinil in Sterile Diluent for FLOLAN® at $T_0$ (A) and $T_{initial}$ (B).
Figure 5B:
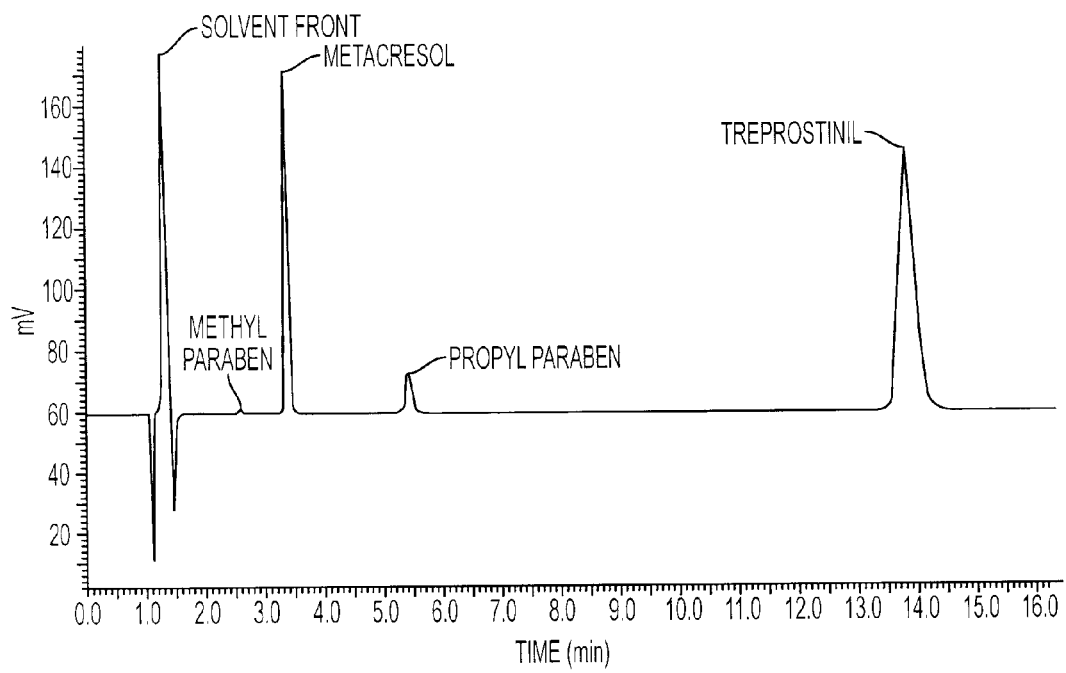
Figure 6:
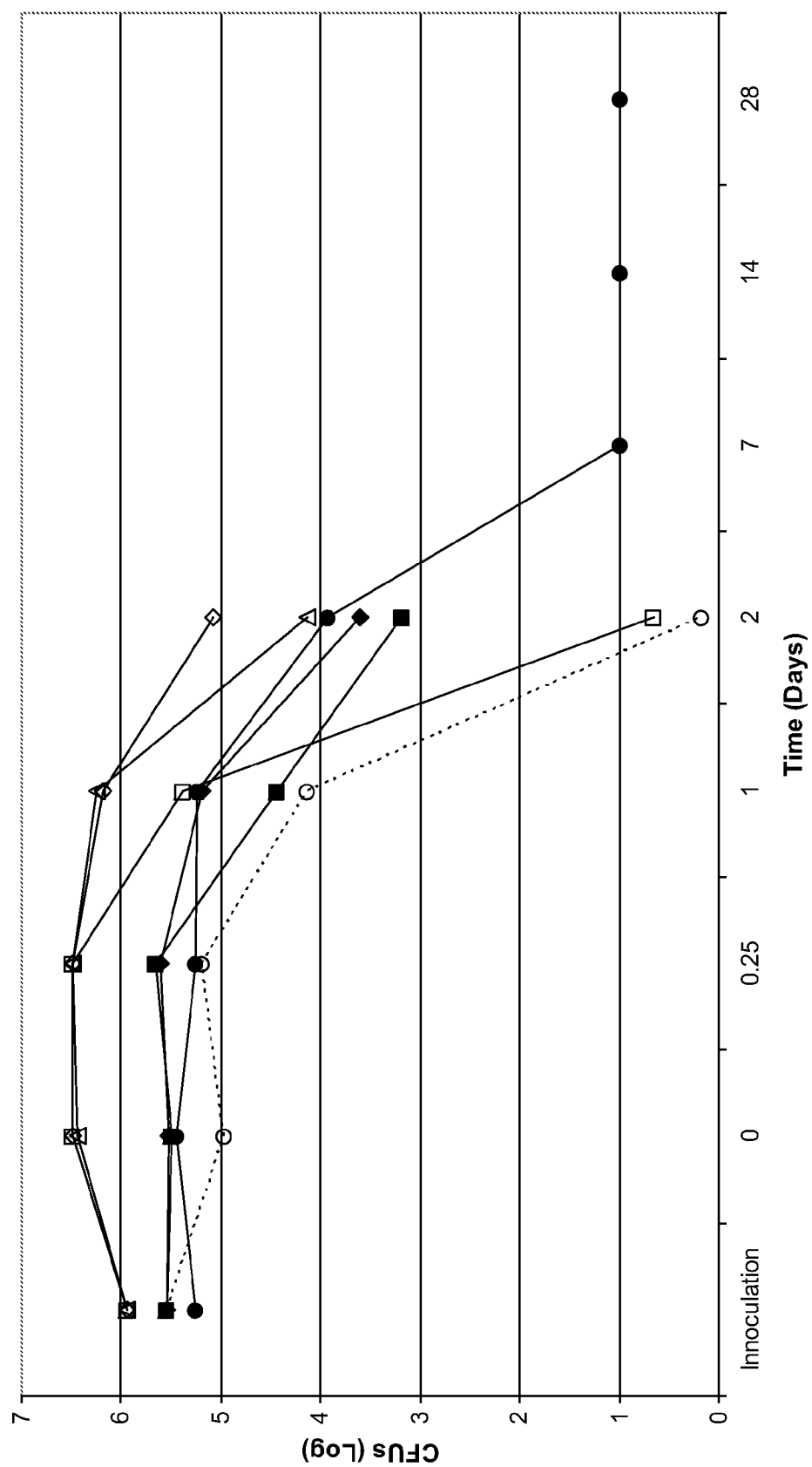
FIG. 6 is a graph showing the antimicrobial activity (CFU) over time (days) of various buffer systems against *Staphylococcus aureus*, a gram positive bacterium, in a pharmaceutical preparation comprising 0.004 mg/mL. Values for ≤Log 1 (treprostinil in sterile diluent) or ≥Log 6.48 (treprostinil in WFI, NS) are recorded as Log 1 and Log 6.48, respectively.

Similar results were obtained for the solutions of treprostinil in Sterile Diluent for FLOLAN®, which are summarized in Table 3. The appearance of all solutions was clear, colorless and free from visible particulate matter. The results also show no compatibility problems for the treprostinil solutions in Sterile Diluent for FLOLAN® for treprostinil at either concentration (FIGS. 4 and 5). Hence, the results show no compatibility problems for the dilute treprostinil solutions in any of the diluent solutions at either concentration.

TABLE 3

Chemical testing results for treprostinil in Sterile Diluent for FLOLAN ®

| Concentration (mg/mL) | Testing | Preparation | $T_0$ | $T_{initial}$ | 24 hours | 52 hours |
|---|---|---|---|---|---|---|
| 0.004 | Treprostinil | 1 | 95.9 | 108.4 | 100.6 | 100.7 |
|  | Assay | 2 | 96.1 | 108.9 | 101.4 | 101.2 |
|  | (% LC) | Average | 96.0 | 108.7 | 101.0 | 101.0 |
|  | pH | NA | 10.6 | 10.5 | 10.6 | 10.5 |
| 0.13 | Treprostinil | 1 | 100.3 | 102.9 | 101.4 | 102.3 |
|  | Assay | 2 | 100.2 | 102.7 | 101.4 | 102.1 |
|  | (% LC) | Average | 100.2 | 102.8 | 101.4 | 102.2 |
|  | pH | NA | 10.5 | 10.4 | 10.5 | 10.5 |

LC: Label claim

For the treprostinil solutions, after 52 hours in the cassette at 40° C./Ambient RH, the solutions were removed and AET was performed according to USP NF 24 Supplement 2<51> with an inclusion of a 48 hour plating for all organisms. For the FLOLAN® solution, the testing was performed following the same procedure, but after the solution had been in the cassette for 8 hours at room temperature. FLOLAN® was also tested for sterility.

The AET USP requirements for a Category 1 product, which includes parenteral solutions, are as follows: for bacteria, there must not be less than a 1.0 log reduction from the initial calculated count at 7 days and not less than a 3.0 log reduction from the initial count at 14 days and no increase from the 14 days' count at 28 days. For the yeast and mold, there should be no increase from the initial calculated count at 7, 14 and 28 days.

While FLOLAN® diluted in sterile diluent for Flolan met the USP requirements for AET, the treprostinil solutions in BWFI and BNS failed. These dilute treprostinil solutions failed AET because the bacterial reduction rate was not sufficient, mainly for gram negative bacteria. However, treprostinil in Sterile Diluent for FLOLAN® met the USP criteria. See FIGS. 6 to 15.

While the invention has been described in connection with specific embodiments thereof, it will be understood that it is capable of further modifications and this application is intended to cover any variations, uses, or alterations of the invention following. In general, the principles of the invention and including such departures from the present disclosure as come within known or customary practice within the art to which the invention pertains and as may be applied to the essential features hereinbefore set forth and as follows in the scope of the appended claims.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention.

What is claimed is:

1. A method of reducing occurrence of a bacterial infection in a human in need of treprostinil, comprising diluting a starting solution comprising the treprostinil with a buffer comprising glycine and having a pH of greater than 10 to provide a final solution comprising the treprostinil with a pH of greater than 10 and administering the final solution to the human in need thereof.

2. The method of claim 1, wherein the administering is by injection.

3. The method of claim 2, wherein the injection is intravenous injection.

4. The method of claim 1, wherein the buffer further comprises sodium hydroxide.

5. The method of claim 1, wherein the buffer has a pH between 10 and 12.

6. The method of claim 5, wherein the buffer has a pH between 10.2 and 10.8.

7. The method of claim 6, wherein the final solution is administered intravenously.

8. The method of claim 1, wherein the final solution is administered at a concentration of the treprostinil between about 0.001 mg/mL to about 1 mg/mL.

9. The method of claim 8, wherein the final solution is administered at a concentration of the treprostinil between about 0.004 mg/mL to about 0.13 mg/mL.

10. The method according to claim 1, wherein the administration reduces the growth of gram negative bacteria.

11. The method of claim 1, wherein the buffer is a 50 mL solution of 94 mg of glycine, 73.3 mg of sodium chloride, and sodium hydroxide.

12. The method of claim 11, wherein the administering is by injection.

13. The method of claim 12, wherein the injection is intravenous injection.

14. The method of claim 1, wherein the treprostinil is treprostinil sodium.

* * * * *